United States Patent
Cotrell

(10) Patent No.: US 8,685,906 B2
(45) Date of Patent: Apr. 1, 2014

(54) LOW IRRITANCY CLEANSING COMPOSITIONS

(75) Inventor: Philip Cotrell, Salisbury, NC (US)

(73) Assignee: Innospec Limited (GB)

( * ) Notice: Subject to any disclaimer, the term of this patent is extended or adjusted under 35 U.S.C. 154(b) by 0 days.

(21) Appl. No.: 13/386,706

(22) PCT Filed: Aug. 2, 2010

(86) PCT No.: PCT/GB2010/051270
§ 371 (c)(1),
(2), (4) Date: Feb. 23, 2012

(87) PCT Pub. No.: WO2011/015858
PCT Pub. Date: Feb. 10, 2011

(65) Prior Publication Data
US 2012/0142572 A1  Jun. 7, 2012

Related U.S. Application Data

(63) Continuation of application No. 61/230,869, filed on Aug. 3, 2009.

(51) Int. Cl.
*C11D 1/02* (2006.01)

(52) U.S. Cl.
USPC .......... 510/126; 510/127; 510/130; 510/136; 510/156; 510/499; 510/506

(58) Field of Classification Search
None
See application file for complete search history.

(56) References Cited

FOREIGN PATENT DOCUMENTS

| WO | 94/09763 A1 | 5/1994 |
| WO | 2005/075623 A1 | 8/2005 |
| WO | 2007/130390 A2 | 11/2007 |

OTHER PUBLICATIONS

International Search Report and Written Opinion in International Application No. PCT/GB2010/051270 mailed Jan. 19, 2012.

*Primary Examiner* — Necholus Ogden, Jr.
(74) *Attorney, Agent, or Firm* — Burns & Levinson, LLP; Janine M. Susan

(57) ABSTRACT

Composition A low irritancy cleansing composition comprises: (a) an anionic surfactant compound of formula (I): wherein $R^1$ represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and M+ represents a cation; (b) an amphoteric surfactant; and (c) an alkoxylated non-ionic species; wherein the molar ratio of component (a) to component (b) is from 0.5:1 to 2:1 and wherein the ratio of the mass of component (c) to the combined mass of components (a) and (b) is less than 1.2:1.

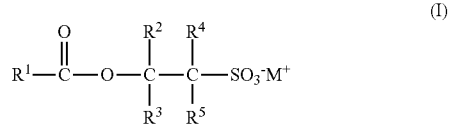

9 Claims, No Drawings

LOW IRRITANCY CLEANSING COMPOSITIONS

CROSS-REFERENCE TO RELATED APPLICATIONS

This application is a U.S. national stage application under 35 U.S.C. 371 of co-pending International Application No. PCT/GB10/51270 filed Aug. 2, 2010 and entitled "COMPOSITION", which in turn claims priority to U.S. Provisional Patent Application No. 61/230,869 filed Aug. 3, 2009, both of which are incorporated by reference herein in their entirety for all purposes.

The present invention relates to low irritancy cleansing compositions, for example compositions suitable for use as baby shampoos, baby baths, mild skin cleansers, mild facial cleansers, cleansers for sensitive skin and the like. Such compositions must exhibit low skin and eye irritation. Low irritancy cleansing compositions of this type may also be useful in animal applications, for example as pet shampoos.

Traditional shampoo formulations often contain polyoxyethylene-alkyl sulphate type anionic surfactants as a major ingredient. However these compounds have been found to cause eye and skin irritation thus limiting their use in products where low irritation is essential, for example in baby shampoos.

Various compositions of the prior art have been prepared to try to provide shampoo formulations having reduced irritancy. These typically comprise combinations of anionic and amphoteric surfactants along with significant levels of non-ionic surfactants.

For example, U.S. Pat. No. 4,177,171 discloses a low irritation shampoo composition comprising 5-20% by weight of a combination of an amphoteric / anionic surfactant complex together with 8-20% by weight of a C16-C18 fatty acid mono ester of sorbitan reacted with 60-80 moles of ethylene oxide.

GB1508929 describes shampoos with a very low eye irritation potential along with excellent foaming and cleansing characteristics based on combinations of an ampholytic 2-alkyl-substituted imidazoline surfactant, a non-ionic surfactant which is one of a certain group of polyoxyethylene-polyoxypropylene block copolymer and an anionic alcohol-ether sulfate surfactant.

CA1077849 relates to high lathering detergent compositions having excellent foam stability and low ocular irritation comprising a betaine surfactant, an anionic surfactant and a polyoxyethylene derivative of a hydrophobic base as a non-ionic surfactant in a weight ratio of about 1:1:3.

CA1080625 describes conditioning and cleansing shampoo compositions which are non-irritating to the eyes and comprise a 1:1 molar ratio complex of an amphoteric surfactant and an anionic surfactant; a non-ionic surfactant; and a cationic quaternary-nitrogen based hydroxycellulose ether polymer.

EP0160269 describes a mild shampoo formulation containing an anionic surfactant, an imidazolinium or sulphosuccinate derivative, an amine oxide derivative and an ethoxylated dihydric or polyhydric alcohol derivative. The combination of an amine oxide derivative and a dihydric or polyhydric alcohol derivative is said to improve the mildness and increase the viscosity of the formulation.

These documents, and others, suggest the use of an ethoxylated non ionic polymer, for example an ethoxylated sorbitan ester, in order to increase the mildness of a shampoo composition. However a major drawback of using ethoxylated surfactants (whether non ionic or otherwise) is that they may contain 1,4-dioxane as an impurity and this has been identified as a carcinogen.

It is an aim of the present invention to provide a cleansing formulation having low skin and ocular irritation and which comprises reduced levels of ethoxylate-containing surfactants.

According to a first aspect of the present invention there is provided a low irritancy cleansing composition comprising:
(a) an anionic surfactant compound of formula (I):

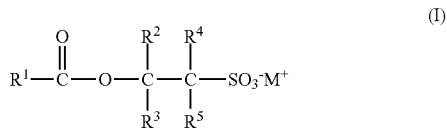

wherein $R^1$ represents a $C_{4-36}$ substituted or unsubstituted hydrocarbyl group;
each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and
$M^+$ represents a cation;
(b) an amphoteric surfactant; and
(c) an alkoxylated non-ionic species;
wherein the molar ratio of component (a) to component (b) is from 0.5:1 to 2:1 and wherein the ratio of the mass of component (c) to the combined mass of components (a) and (b) is less than 1.2:1.

Component (a) comprises an anionic surfactant compound of formula (I):

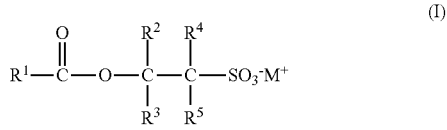

Preferably $R^1$ is selected from a substituted or unsubstituted alkyl, alkenyl, aryl or alkylaryl group. More preferably $R^1$ is selected from a substituted or unsubstituted alkyl or alkenyl group. Most preferably $R^1$ is an unsubstituted alkyl or alkenyl group, especially an unsubstituted alkyl group.

Preferably $R^1$ represents a $C_{5-30}$ alkyl group, preferably a $C_{7-24}$ alkyl group, more preferably a $C_{7-21}$ alkyl group, most preferably a $C_{7-17}$ alkyl group.

Preferably $R^2$ represents a $C_{1-4}$ alkyl group, suitably a $C_{1-4}$ alkyl group in which a propyl or butyl group, when present, is straight-chained. Preferably $R^2$ represents an n-propyl, ethyl or, most preferably, a methyl group.

Preferably $R^3$ represents a hydrogen atom.

Preferably one of $R^4$ and $R^5$ represents a hydrogen atom and the other represents a hydrogen atom or a $C_{1-4}$ alkyl group. Preferably one of $R^4$ and $R^5$ represents a hydrogen atom or a $C_{1-4}$ alkyl group in which a propyl or butyl group is straight-chain. Preferably one of $R^4$ and $R^5$ represents an n-propyl, ethyl or methyl group or, most preferably, a hydrogen atom. Most preferably both $R^4$ and $R^5$ represent hydrogen atoms.

In some embodiments the present invention may include a mixture of more than one compound of formula (I). For example an isomeric mixture of compounds of formula (I) may be present. Such a mixture may include, for example a compound in which $R^2$ is alkyl (suitably methyl) and $R^3$, $R^4$ and $R^5$ are all hydrogen and a compound in which $R^5$ is is alkyl (suitably methyl) and $R^2$, $R^3$ and $R^4$ are all hydrogen.

Preferably $M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium and potassium cations, and alkaline earth metal cations, for example calcium and magnesium cations. Preferably $M^+$ represents a potassium cation, or, especially, a sodium cation.

$R^1$ may be an alkyl group or an alkenyl group. Preferably $R^1$ is an alkyl group. In some embodiments the component surfactant of the present invention may comprise a mixture of fatty acids to form a mixture of compounds of formula (I) in which $R^1$ may be different.

$R^1$ is preferably the residue of a fatty acid. Fatty acids obtained from natural oils often include mixtures of fatty acids. For example the fatty acid obtained from coconut oil contains a mixture of fatty acids including $C_{12}$ lauric acid, $C_{14}$ myristic acid, $C_{16}$ palmitic acid, $C_8$ caprylic acid, and $C_{18}$ stearic and oleic.

$R^1$ may include the residue of one or more naturally occurring fatty acids and/or of one or more synthetic fatty acids. In some preferred embodiments $R^1$ consists essentially of the residue of a single fatty acid.

Examples of carboxylic acids from which $R^1$ may be derived include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, erucic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Most preferably $R^1$ comprises the residue of lauric acid, that is a saturated fatty acid having 12 carbon atoms or the residue of mixed fatty acids derived from coconut oil.

The compound of formula (I) may be prepared by any of the methods disclosed in the prior art, for example see the methods described in WO94/09763 and WO2005/075623.

In especially preferred embodiments, $R^3$, $R^4$ and $R^5$ are all hydrogen and $R^2$ is ethyl or, most preferably methyl.

In such preferred embodiments the composition of the present invention preferably comprises the reaction product of sodium methyl isethionate and a fatty acid, that is a compound of formula (II):

$$R^1 \underset{O}{\overset{O}{\|}}\!\!-\!\!O\!\!-\!\!\underset{R^3}{\overset{R^2}{|}}\!\!-\!\!SO_3^- M^+ \quad (II)$$

in which one of $R^2$ and $R^3$ is methyl and the other is hydrogen. Mixtures of these isomers may be present.

In some embodiments the composition of the present invention comprises one or more of sodium lauroyl methyl isethionate, sodium cocoyl methyl isethionate and sodium oleoyl methyl isethionate.

Most preferably the composition of the present invention comprises sodium lauroyl, methyl isethionate and/or sodium cocoyl methyl isethionate, Sodium lauroyl methyl isethionate is especially preferred.

Component (b) comprises an amphoteric surfactant.

By amphoteric surfactant we mean to include any surfactants having the ability to exhibit both positive and negative sites. The surfactant component (b) may be selected from surfactants referred to as betaines, including sultaines (sulphobetaines), or other zwitterionic or amphoteric surfactants, for example those based on fatty nitrogen derivates.

Suitable surfactants for use as component (b) may be selected from betaines, for example alkyl betaines, alkylamidopropyl betaines, alkylamidopropyl hydroxy sultaines, alkylampho acetates, alkylamphodiacetates, alkylamphopropionates, alkylamphod ipropionates, alkyliminodipropionates and alkyliminodiacetates.

Surfactants for use as component (b) in the compositions of the present invention may include those which have an alkyl or alkenyl group of 7 to 22 carbon atoms and comply with an overall structural formula:

$$R^1\!\!-\!\!\!\left[\!\!\underset{}{\overset{O}{\overset{\|}{C}}}\!\!-\!\!NH(CH_2)_m\!\!\right]_{\!\!n}\!\!-\!\!\underset{R^3}{\overset{R^2}{\underset{|}{\overset{|}{N^+}}}}\!\!-\!\!X\!\!-\!\!Y^-$$

where $R^1$ is alkyl or alkenyl of 7 to 22 carbon atoms; $R^2$ and $R^3$ are each independently alkyl, hydroxyalkyl or carboxyalkyl of 1 to 6 carbon atoms; m is 2 to 4; n is 0 or 1; X is alkylene of 1 to 6 carbon atoms optionally substituted with hydroxyl; and Y is $-CO_2$ or $-SO_3$.

Surfactants suitable for use as component (b) may include simple betaines of formula:

$$R^1\!\!-\!\!\underset{R^3}{\overset{R^2}{\underset{|}{\overset{|}{N^+}}}}\!\!-\!\!CH_2CO_2^-$$

and amido betaines of formula:

$$R^1\!\!-\!\!\overset{O}{\overset{\|}{C}}\!\!-\!\!NH(CH_2)_m\!\!-\!\!\underset{R^3}{\overset{R^2}{\underset{|}{\overset{|}{N^+}}}}\!\!-\!\!CH_2CO_2^-$$

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the groups $R^1$ has 10 to 14 carbon atoms. $R^2$ and $R^3$ are preferably methyl.

Surfactant component (b) may include sultaines (or sulphobetaines) of formula:

$$R^1\!\!-\!\!\underset{R^3}{\overset{R^2}{\underset{|}{\overset{|}{N^+}}}}\!\!-\!\!(CH_2)_3SO_3^- \qquad R^1\!\!-\!\!\overset{O}{\overset{\|}{C}}\!\!-\!\!NH(CH_2)_m\!\!-\!\!\underset{R^3}{\overset{R^2}{\underset{|}{\overset{|}{N^+}}}}\!\!-\!\!(CH_2)_3SO_3^-$$

where m is 2 or 3, or variants of these in which
  $-(CH_2)_3SO_3^-$ is replaced by $$-CH_2\!\!-\!\!\underset{}{\overset{OH}{\underset{|}{CH}}}\!\!-\!\!CH_2SO_3^-$$

where $R^1$, $R^2$ and $R^3$ in these formulae are as defined previously.

Surfactant component (b) may include amphoacetates and diamphoacetates. Amphoacetates generally conform to the following formula:

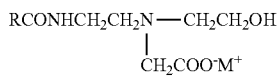

Diamphoacetates generally conform to the following formula:

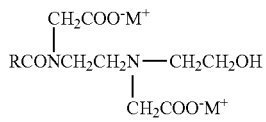

where R is an aliphatic group of 8 to 22 carbon atoms and M is a cation such as sodium, potassium, ammonium, or substituted ammonium.

Suitable acetate-based amphoteric surfactants include lauroamphoacetate; alkyl amphoacetate; cocoampho(di)acetate; cocoamphoacetate; disodium cocoamphodiacetate; sodium cocoamphoacetate; disodium cocoamphodiacetate; disodium capryloamphodiacete; disodium lauroamphoacetate; sodium lauroamphoacetate and disodium wheatgermamphodiacetate.

Suitable betaine surfactants include alkylamido betaine; alkyl betaine, $C_{12/14}$ alkyldimethyl betaine; cocoamidopropylbetaine; tallow bis(hydroxyethyl) betaine; hexadecyldimethylbetaine; cocodimethylbetaine; alkyl amido propyl sulfo betaine; alkyl dimethyl amine betaine; coco amido propyl dimethyl betaine; alkyl amido propyl dimethyl amine betaine; cocamidopropyl betaine; lauryl betaine; laurylamidopropl betaine, coco amido betaine, lauryl amido betaine, alkyl amino betaine; alkyl amido betaine; coco betaine; lauryl betaine; diemethicone propyl PG-betaine; oleyl betaine; N-alkyldimethyl betaine; coco biguamide derivative, $C_8$ amido betaine; $C_{12}$ amido betaine; lauryl dimethyl betaine; alkylamide propyl betaine; amido betaine; alkyl betaine; cetyl betaine; oleamidopropyl betaine; isostearamidopropyl betaine; lauramidopropyl betaine; 2-alkyl-N-carboxymethyl-N-hydroxyethyl imidazolinium betaine; 2-alkyl-N-carboxyethyl-N-hydroxyethyl imidazolinium betaine; 2-alkyl-N-sodium carboxymethyl-N-carboxymethyl oxyethyl imidazolinium betaine; N-alkyl acid amidopropyl-N,N-dimethyl-N-(3-sulfopropyl)-ammonium-betaine; N-alkyl-N,N-dimethyl-N-(3-sulfopropyl)-ammonium-betaine; cocodimethyl betaine; apricotamidopropyl betaine; isostearamidopropyl betaine; myristamidopropyl betaine; palmitamidopropyl betaine; cocamidopropyl hydroxy sultaine; undecylenamidopropyl betaine; cocoamidosulfobetaine; alkyl amido betaine; $C_{12/18}$ alkyl amido propyl dimethyl amine betaine; lauryldimethyl betaine; ricinol amidobetaine; tallow aminobetaine.

Suitable glycinate-based amphoteric surfactants include cocoamphocarboxyglycinate; tallowamphocarboxygycinate; capryloamphocarboxyglycinate, oleoamphocarboxyglycinate, bis-2-hydroxyethyl tallow glycinate; lauryl amphoglycinate; tallow polyamphoglycinate; coco amphoglycinate; oleic polyamphoglycinate; N-$C_{10/12}$ fatty acid amidoethyl-N-(2-hydroxyethyl)-glycinate; N-$C_{12/18}$-fatty acid amidoethyl-N-(2-hydroxyethyl)-glycinate; dihydroxyethyl tallow glycinate.

Preferred acetate-based amphoteric surfactants for use as component (b) include sodium lauroamphoacetate, disodium lauroamphoacetate and mixtures thereof.

Preferred betaine surfactants for use as component (b) include cocoamidopropyl betaine.

Preferred sultaine surfactants for use as component (b) include cocoamidopropylhydroxy sultaine.

Component (c) comprises an alkoxylated non-ionic species. This may be a non-ionic surfactant or other alkoxylated compound, for example a polymeric compound. Preferably the alkoxylated non-ionic species comprises at least two alkoxy residues, preferably at least two ethoxy residues.

Suitable alkoxylated non-ionic surfactants include any compound comprising one or more alkylene oxide residue and a hydrophobic group. Preferred non-ionic surfactants are compounds which include one or more ethylene oxide and/or propylene oxide residue and a hydrophobic group. Suitable non-ionic surfactants may be formed by the reaction of aliphatic alcohols, acids, amides or alkyl phenols with alkylene oxides. Preferably the hydrophobic group comprises a hydrocarbon chain having at least 4 carbon atoms, preferably at least 5 carbon atoms, more preferably at least 6 carbon atoms. Preferably the hydrophobic group comprises from 6 to 30 carbon atoms, more preferably from 6 to 21 carbon atoms, most preferably from 8 to 18 carbon atoms. Preferably the hydrophobic group is an alkyl group. The non-ionic surfactant component (c) may include more than one hydrophobic residue.

Alternatively the alkoxylated non-ionic species may be a polymeric species, for example an ethylene oxide-propylene oxide copolymer, suitably a block copolymer. Such compounds will be well known to the person skilled in the art as polaxomer compounds and are for example available from BASF under the trade mark Pluronic.

Suitable non-ionic surface-active agents may be selected from the following: reaction products of compounds having a hydrophobic group and a reactive hydrogen atom, for example aliphatic alcohols, acids, amides or alkyl phenols with alkylene oxides, especially ethylene oxide either alone or with propylene oxide (for example alkyl ($C_6$-$C_{22}$) phenol-ethylene oxide condensates, the condensation products of aliphatic ($C_8$ -$C_{18}$) primary or secondary linear or branched alcohols with ethylene oxide, and products made by condensation of ethylene oxide with the reaction products of propylene oxide and ethylenediamine); and sorbitan ester alkoxylates. Preferred non-ionic surfactants include alkoxylated fatty alcohols, alkoxylated fatty acids, alkoxylated glycerol esters and alkoxylated sorbitan esters, especially ethoxylated species and especially those including lauryl, cetylstearyl, stearyl, cetyl and oleocetyl residues.

Preferably the non-ionic surfactant comprises at least 20 alkylene oxide residues, preferably at least 40, for example at least 60.

Preferred non-ionic surfactants for use as component (c) are those which are formed by the reaction of a compound including a hydrophobic group and ethylene oxide.

One suitable class of non-ionic surfactants are polyethylene sorbitan fatty acid esters with the esterifying fatty acid being selected from the group consisting of $C_{12}$-$C_{18}$ fatty acids wherein an average of about 1 or 3 of said acids are esterified per polyoxyethylene sorbitan molecule. One preferred non-ionic surfactant is a mixture of laurate esters of sorbitol and sorbitol anhydrides (sorbitan) consisting predominantly of the mono-ester condensed with about 20 moles of ethylene oxide. This surfactant is designated in the CTFA dictionary as Polysorbate 20 and is also known in the art as polyoxyethylene (20) sorbitan monolaurate and is available from several commercial sources.

Another suitable example of a polyoxyethylene alkyl ester is the CTFA designated Polysorbate 80 which is a mixture of oleate esters of sorbitol and sorbitol anhydrides, condensed with approximately 80 moles of ethylene oxide.

The ratio of the mass of component (c) to the combined mass of components (a) and (b) is less than 1.2:1. Preferably it is less than 1.1:1, preferably less than 1:1, more preferably less than 0.9:1, suitably less than 0.8:1, more preferably less than 0.75:1 for example less than 0.6:1 or less than 0.5:1.

The composition of the present invention may comprise further surfactant components in addition to components (a), (b) and (c). Such surfactants may be selected from anionic surfactants, cationic surfactants, amphoteric surfactants, non-ionic surfactants and mixtures thereof. Cationic surfactants, for example quaternary ammonium compounds may be used as conditioning agents. The selection of suitable further surfactants for use in the composition of the present invention is within the competence of the person skilled in the art. When such additional surfactant components are present it is preferred that these surfactants do not include alkylene oxide residues.

In preferred embodiments components (a), (b) and (c) together comprise at least 70 wt % of all surfactants present in the composition, preferably at least 75 wt %, more preferably at least 80 wt %, suitably at least 85 wt %, more preferably at least 90 wt %, preferably at least 95 wt % and most preferably at least 98 wt %.

Preferably component (c) comprises less than 60 wt % of all surfactants present in the composition, preferably less than 50 wt %, more preferably less than 40 wt %, preferably less than 30 wt %, for example less than 25 wt % or less than 20 wt %. Component (c) may comprise less than 15 wt % of all surfactants present in the composition, less than 10 wt % or less than 5 wt %.

The molar ratio of component (a) to component (b) is between 0.5:1 and 2:1. Preferably it is between 0.6:1 and 1.8:1, more preferably between 0.7:1 and 1.7:1, preferably between 0.8:1 and 1.4:1, more preferably between 0.85:1 and 1.3:1, most preferably between 0.9:1 and 1.2:1.

Component (a) is preferably present in the cleansing composition of the present invention in an amount of at least 0.5 wt %, preferably at least 1 wt %, for example at least 1.5 wt %, suitably at least 2 wt % or at least 2.5 wt %. Component (a) may be present in an amount of up to 50 wt %, preferably up to 40 wt %, suitably up to 30 wt %, preferably up to 20 wt %, more preferably up to 10 wt %, for example up to 7.5 wt % or up to 5 wt %.

Component (b) is preferably present in the cleansing composition of the present invention in an amount of at least 0.5 wt %, preferably at least 1 wt %, for example at least 1.5 wt %, suitably at least 2 wt % or at least 2.5 wt %. Component (b) may be present in an amount of up to 50 wt %, preferably up to 40 wt %, suitably up to 30 wt %, preferably up to 20 wt %, more preferably up to 10 wt %, for example up to 7.5 wt % or up to 5 wt %.

Component (c) is preferably present in the cleansing composition of the present invention in an amount of at least 0.5 wt %, preferably at least 1 wt %, for example at least 1.5 wt %, suitably at least 2 wt % or at least 2.5 wt %. Component (c) may be present in an amount of up to 50 wt %, preferably up to 40 wt %, suitably up to 30 wt %, preferably up to 20 wt %, more preferably up to 10 wt %, for example up to 7.5 wt % or up to 5 wt %.

The skilled person will appreciate that commercially available sources of surfactants often include significant levels of impurities. The levels of impurity present in commercial surfactants may be up to 25% by weight or even up to 30% by weight and these impurities usually contain unreacted starting materials and/or by-products.

For the avoidance of doubt, unless otherwise stated, any definitions of amounts of surfactant stated herein and molar and weight ratios thereof refer to the actual amount of active surfactant compound present in the composition.

As mentioned above, each of components (a), (b) and (c) may comprise a mixture of the specified surfactant and any amount mentioned in this specification refers to the total amount of each such surfactant type present in the composition. As will be readily understood by the skilled person, commercial sources of surfactant often comprise mixtures of active surfactant compounds (as well as impurities), for example different isomers, especially if they have been prepared from natural sources, for example fatty acid mixtures found in nature.

The composition of the present invention may comprise one or more further components selected from conditioning agents, antibacterial agents, foam boosters, pearlescers, perfumes, dyes, colouring agents, preservatives, thickeners, proteins, polymers such as silicone polymers, phosphate esters, sunscreens, antidandruff agents, buffering agents, moisturisers such as fatty acid alkanolamides, silicone derivatives, cationic polymers, propylene glycol, glycerine, viscosity controlling agents such as methyl cellulose, and other additives which usually used for cleansers.

Suitable conditioning agents include quaternary ammonium compounds of formula

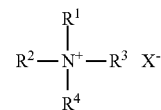

wherein each of $R^1$, $R^2$, $R^3$ and R4 is an alkyl or alkenyl group and X is chloride, bromide or methyl sulfate. At least one of $R^1$, $R^2$, $R^3$ and $R^4$ is a $C_6$ to $C_{24}$ alkyl or alkenyl group and the others are $C_1$ to $C_4$ alkyl, for example methyl. In some embodiments two, three or four of the groups $R^1$, $R^2$, $R^3$ and $R^4$ may be $C_6$ to $C_{24}$ alkyl or alkenyl.

Suitable conditioning agents for use herein include those designated as polyquaterniums on the INCI list, for example polyquaternium-10 and polyquaternuim-7; as well as guar hydroxypropyl ammonium chloride and similar cationic polymers.

Suitable preservatives include dimethyl dimethylolhydantoin (DMDMH), DMDMH/iodopropynyl-butyl carbamate (Glydant Plus, a registered trademark of Lonza Inc.), benzyl alcohol, methyl paraben, propyl paraben and imidazolidinyl urea. Of course there are many additional preservatives that will function effectively in cleansing compositions such as shampoos.

Suitably the cleansing composition of the present invention has a pH of from 4 to 8, preferably from 4.5 to 7, for example from 4.5 to 6. The pH can be adjusted, as needed, with either a base for example sodium hydroxide or sodium carbonate or an acid for example citric acid, succinic acid, or phosphoric acid.

The present invention is preferably an aqueous composition. In some embodiments the composition may comprise one or more further solvents in addition to water. Such suitable co-solvents may include polar compounds for example alcohols, glycols and the like.

However in preferred embodiments water is the major solvent present in the composition of the present invention and suitably comprises at least 80 wt % of all solvents present, preferably at least 90 wt %, more preferably at least 95 wt %.

The present invention provides a low irritancy cleansing composition. Preferably the composition of the present invention is very low irritating to both the skin and the eyes.

The cleansing composition may be used for any purpose in which low irritancy to the skin and/or eyes is desirable. For example the composition may be used as a facial wash or a product for people with sensitive skin. Most preferably the composition of the present invention is a baby care product, for example a baby bath product or a baby shampoo.

Suitably the cleansing composition of the present invention is sufficiently non-irritating to enable it to be used as a baby shampoo.

It is desired to minimise the concentration of component (c) present in the composition of the present invention. A suitable concentration may be determined empirically by preparing a composition comprising the desired amounts of components (a) and (b) and the adding incremental amounts of component (c) until a desired low level of ocular irritation is achieved.

Ocular irritation can be measured by any suitable method and such methods will be known to the person skilled in the art. A standard method known since 1944 is the Draize Eye Irritancy Test. This is a long established test which involves delivery of a material into the conjunctival sac of one eye of a rabbit. However this test is now used less often as it is often considered cruel and alternative in vitro tests have been developed. One suitable method is the "EpiOcular"® of MatTek. This corneal model consists of normal, human-derived epidermal keatinocytes which have been cultured to form a stratified, squamous epithelium similar to that found in the cornea. The epidermal cells, which are cultured on specially prepared cell culture inserts using serum free medium, differentiate to form a multilayered structure which closely parallels the corneal epithelium. The system is said to provide a predictive, morphologically relevant in vitro means to assess ocular irritancy. The results from the EpiOculuar® test allow a composition to be classified as severely irritating, moderately irritating, mildly irritating or minimally or non-irritating. Such a test is used in the examples.

Suitably the low irritancy cleansing formulation of the present invention would be classified as mildly irritating, minimally irritating or non-irritating on the EpiOcular® test. Preferably it would be classified as non-irritating or minimally irritating.

Details of the EpiOcular® test can be found in the paper entitled "Evaluation of the EpiOcular™ Tissue Model as an Alternative to the Draize Eye Irritation Test"; M. Stern, M. Klausner, R. Alvarado, K. Renskers, M. Dickens; *Toxicology in Vitro*, Volume 12, Issue 4, August 1998, Pages 455-461.

As mentioned above a number of in vitro eye irritancy tests are available. Many of these tests allow the results to be correlated to provide an equivalent score on the Draize test. In order to allow a correlation to be made it is often necessary to carefully select appropriate conditions, especially concentration. However the performance of such a test would be well within the competence of the skilled person.

The composition of the present invention would preferably be such that when testing using in vitro tests of this type it would provide a score equivalent to mild or non-irritating on the Draize Test.

Preferably the cleansing composition of the present invention has low skin irritancy. Skin irritancy may be measured by any suitable means. In one common method a composition is applied to the skin for 14 consecutive days and the irritation evaluated in what is referred to as a 14-Day Cumulative Irritation Test.

The low irritancy cleansing composition of the present invention is very mild and can thus be used as a baby shampoo, baby bath, mild skin cleanser, facial cleanser, sensitive skin cleanser and the like. The composition is particularly advantageous as it contains lower levels of ethoxylated nonionic surfactants than have been previously used and thus any 1,4-dioxane will be present in a lower amount.

The low irritancy cleansing composition of the present invention could also be used in animal care applications, for example as a pet shampoo.

According to a second aspect of the present invention there is provided a concentrated surfactant composition which upon dilution forms a low irritancy cleansing composition of the first aspect of the present invention.

Preferred features of the second aspect are as defined in relation to the first aspect. The invention is further illustrated with reference to the following examples.

EXAMPLES

The compositions prepared were as follows:

|   |   | Example 1 | Example 2 | Example 3 (of the invention) | Example 4 (of the invention) |
|---|---|---|---|---|---|
| A | ISELUX 20% Active SLMI Aq. Soln | 50 wt % | | 25 wt % | 25 wt % |
| B-1 | Sodium Lauroamphoacetate 30% Active | | 33.33 wt % | 16.67 wt % | |
| B-2 | Cocamidopropyl Betaine 30% Active | | | | 16.67 wt % |
| C | PEG-80 Sorbitan Monolaurate 70% Active | | | 14.29 | 14.29 wt % |
|   | NATRLQUEST E-30- trisodium EDDS chelant, 40% Active | 0.9 wt % | 0.9 wt % | 0.9 wt % | 0.9 wt % |
|   | Deionised Water | 49.1 wt % | 65.77 wt % | 43.14 wt % | 43.14 wt % |
|   | 50% Citric Acid (to achieve pH 6.0) | QS | QS | QS | QS |

-continued

|  | Example 1 | Example 2 | Example 3 (of the invention) | Example 4 (of the invention) |
|---|---|---|---|---|
| % Active SLMI - A | 10 wt % |  | 5 wt % | 5 wt % |
| % Active Amphoacetate - B-1 or Betaine B-2 |  | 10 wt % | 5 wt % | 5 wt % |
| % Active Non-ionic - C |  |  | 10 wt % | 10 wt % |
| Molar Ratio A/B | N/A | N/A | 1.0/0.97 | 1.0/1.05 |
| Ratio of (A + B)/C (by weight, active basis) | N/A | N/A | 1/1 | 1/1 |

SLMI is sodium lauroyl methyl isethionate.

The compositions were tested, as 10 wt % dilutions in water, using the EPIOCULAR in vitro test described above. The results were as follows:

Calculated Draize Scores

| Example 1 | Example 2 | Example 3 (of the invention) | Example 4 (of the invention) |
|---|---|---|---|
| 10.8 | 3.2 | 2.0 | 2.2 |

The correlation between calculated scores and irritation category is shown below

| Calculated Draize Score | Irritation Category |
|---|---|
| 0-15 | Non Irritating (0 score)/Minimal |
| 15.1-25 | Mild |
| 25.1-50 | Moderate |
| 50.1-110 | Severe/Extreme |

The irritation studies show that all of the formulas were minimally irritating, but that the combinations of the invention were less irritating than the SLMI alone.

ISELUX, NATRLQUEST and EPIOCULAR are registered trade marks.

The invention claimed is:

1. A low irritancy cleansing composition comprising:
(a) 0.5 to 5% of an anionic surfactant compound of formula (I):

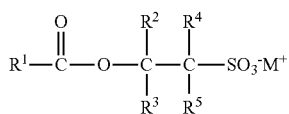

(I)

wherein $R^1$ represents a $C_{4-36}$ substituted or unsubstituted hydrocarbyl group;
each of $R^2$, $R^3$, $R^4$ and $R^5$ independently represents a hydrogen atom or a $C_{1-4}$ alkyl group and wherein at least one of $R^2$, $R^3$, $R^4$, and $R^5$ is not hydrogen and
$M^+$ represents a cation;
(b) 0.5 to 7.5 wt % of an amphoteric surfactant; and
(c) an alkoxylated non-ionic species;
wherein the molar ratio of component (a) to component (b) is from 0.5:1 to 1.3:1 and
wherein the ratio of the mass of component (c) to the combined mass of components (a) and (b) is less than 1.2:1; and wherein component (c) comprises at least two alkoxy residues.

2. The composition according to claim 1 wherein ratio of the mass component (c) to the combined mass of components (a) and (b) is less than 0.7:1.

3. The composition according to claim 1 wherein component (a) is selected from the group consisting of sodium lauroyl methyl isethionate, sodium cocoyl methyl isethionate, sodium oleoyl methyl isethionate and a mixture thereof.

4. The composition according to claim 1 wherein component (b) is selected from the group consisting of a betaine, an alkylamphoacetate, an alkylamphodiacetate, an alkylamphopropionate, an alkylamphodipropionate, an alkyliminoacetate, an alkyliminopropionate and mixtures thereof.

5. The composition according to claim 4 wherein component (b) is selected from the group consisting of sulphobetaine, cocoamidopropyl betaine, cocoamidopropylhydroxy sultaine, sodium lauroamphoacetate, disodium lauroamphoacetate and mixtures thereof.

6. The composition according to claim 1 wherein component (c) comprises an ethoxylated non-ionic species.

7. The composition according to claim 1 claim which is classified as mildly irritating on the EpiOcular (RTM) test.

8. The composition according to claim 1 which exhibits mild or no skin irritancy on a 14 day cumulative irritation test.

9. The composition according to claim 1 which is selected from the group consisting of a baby shampoo, a baby bath, a mild skin cleaner, a facial cleanser and a sensitive skin cleanser.

* * * * *

UNITED STATES PATENT AND TRADEMARK OFFICE
CERTIFICATE OF CORRECTION

PATENT NO. : 8,685,906 B2  Page 1 of 1
APPLICATION NO. : 13/386706
DATED : April 1, 2014
INVENTOR(S) : Cotrell It is certified that error appears in the above-identified patent and that said Letters Patent is hereby corrected as shown below:

On the title page, Item [63] Related U.S. Application Data, "Continuation of" should read
-- Provisional --

In the Claims

Column 11, line 47 claim 1, "0.5 to 5%" should read -- 0.5 to 5 wt% --

Column 12, line 48 claim 7, "claim 1 claim" should read -- claim 1 --

Signed and Sealed this
Tenth Day of June, 2014

Michelle K. Lee
*Deputy Director of the United States Patent and Trademark Office*